United States Patent [19]

Urban

[11] Patent Number: 5,010,185
[45] Date of Patent: Apr. 23, 1991

[54] PROCESSES FOR TIGOGENIN BETA-CELLOBIOSIDE

[75] Inventor: Frank J. Urban, Waterford, Conn.

[73] Assignee: Pfizer Inc., New York, N.Y.

[21] Appl. No.: 365,588

[22] Filed: Jun. 13, 1989

[51] Int. Cl.$^5$ .................... C07J 53/00; C07H 15/24; C07H 1/00
[52] U.S. Cl. ..................... 536/6.1; 536/4.1; 536/5; 536/6; 536/18.5; 514/824
[58] Field of Search ............. 536/4.1, 18.1, 18.2, 536/18.4, 18.7, 55.3, 5.6, 6.1, 17.9, 18.5

[56] References Cited

U.S. PATENT DOCUMENTS 4,602,003 7/1986 Malinow .............................. 514/26
4,602,005 7/1986 Malinow .............................. 514/26

OTHER PUBLICATIONS

Liotta et al., J. Am. Chem. Soc., vol. 111, pp. 783–785 (1989).
Malinow et al., Steroids 48, 197–211 (1986).
Schmidt, Agnew. Chemie. Int. Ed. Eng. 25, 212–235 (1986).
Schmidt et al., ibid., 19, 731–732 (1980).
Schmidt et al., ibid., 21, 72–73 (1982).

*Primary Examiner*—Ronald W. Griffin
*Assistant Examiner*—Nancy S. Carson
*Attorney, Agent, or Firm*—Peter C. Richardson; J. Trevor Lumb; Robert K. Blackwood

[57] ABSTRACT

Improved processes for the synthesis of tigogenin beta-cellobioside, a known hypocholesterolemic agent, using cellobiose heptaacetate and tigogenin as starting materials.

14 Claims, No Drawings

PROCESSES FOR TIGOGENIN BETA-CELLOBIOSIDE

BACKGROUND OF THE INVENTION

The present invention is directed to novel and advantageous processes for the synthesis of tigogenin beta-cellobioside and to certain novel intermediates used in these processes.

Tigogenin beta-cellobioside is a known compound having utility in the treatment of hypercholesterolemia and atherosclerosis (Malinow, U.S. Pat. Nos. 4,602,003 and 4,602,005; Malinow et al. Steroids, vol. 48, pp. 197-211, 1986). Each patent discloses a different synthesis of this compound from beta-cellobiose octaacetate; the first via the glycolyl bromide heptaacetate which is coupled with tigogenin in the presence of silver carbonate, and finally hydrolyzed; and the second direct stannic chloride catalyzed coupling of the octaacetate with tigogenin in methylene chloride, again followed by hydrolysis. In Malinow et al., reaction of cellobiose octaacetate with titanium tetrabromide gave the glycosyl bromide heptaacetate, which was coupled with tigogenin by means of mercuric cyanide, and then hydrolyzed. All of these methods have serious drawbacks for producing bulk material. A desirable goal, met by the present invention, has been to devise synthetic methods which avoid toxic and/or expensive reagents, and which cleanly produce the desired tigogenin betacellobioside, avoiding tedious and expensive purification steps.

Schmidt, Angew. Chem. Int. Ed. Engl., v. 25, pp. 212-235 (1986) has reviewed the synthesis and reactions of O-glycosyl trichloroacetimidates formed by the reaction of sugars possessing a 1-OH group (but with other hydroxy groups protected, e.g., by benzyl or acetyl) with trichloroacetonitrile in the presence of a base. There is preferential formation of the alpha-anomer when NaH is used as base, and preferential formation of the beta-anomer when the base is $K_2CO_3$. The alpha anomer of tetrabenzylglucosyl trichloroacetimidate when coupled with cholesterol gave anomeric mixtures which varied with catalyst (p-toluenesulfonic acid or boron trifluoride etherate) and temperature ($-40°$ to $+20°$ C.). On the other hand, both the alpha and beta anomers of tetraacetylglucosyl analog reportedly yield exclusively beta-anomeric products.

SUMMARY OF THE INVENTION

The present invention is directed to intermediate compounds of the formula

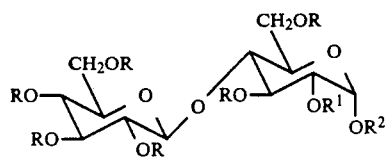

wherein
R is $R^4CO$;
$R^1$ and $R^2$ are taken separately, $R^1$ is $R^4CO$, and $R^2$ is

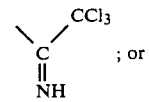

; or $R^1$ and $R^2$ are taken together and are

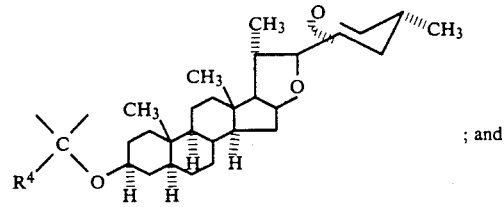

; and $R^4$ is $(C_1-C_4)$alkyl.

Of particular value are those compounds wherein $R^4$ is methyl, i.e., R is acetyl.

The present invention is also directed to over-all processes and certain individual process steps used for the present syntheses of tigogenin beta-cellobioside, as follows:

(a) reacting a cellobiose heptaalkanoate of the formula

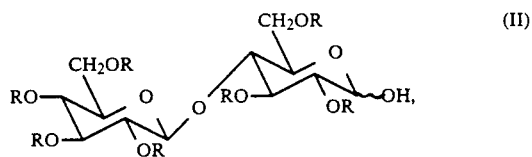

wherein
R is $R^4CO$ and $R^4$ is $(C_1-C_4)$alkyl, with trichloroacetonitrile in the presence of a catalytic amount of cesium carbonate in a reaction-inert solvent at or about ambient temperature to form an imidate of the formula (I) wherein $R^1$ and $R^2$ are taken together, i.e., of the formula

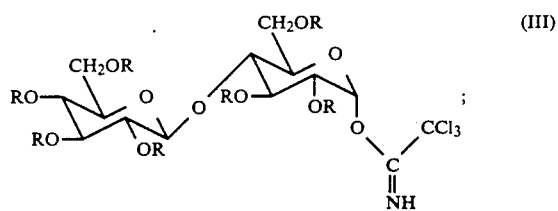

either (b) reacting said imidate with tigogenin in the presence of zinc bromide or magnesium bromide etherate in the same or another reaction-inert solvent at or about ambient temperature to form an orthoester of the formula (I) wherein $R^1$ and $R^2$ are taken together, i.e., of the formula

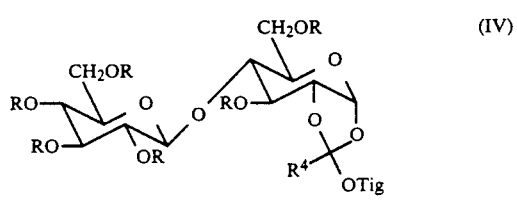

wherein Tig is

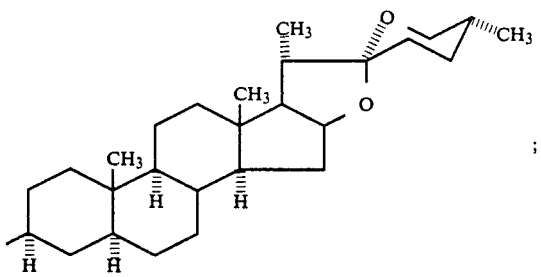

followed by heating said orthoester in the same or another reaction-inert solvent to form a tigogenin beta-cellobioside heptaalkanoate of the formula

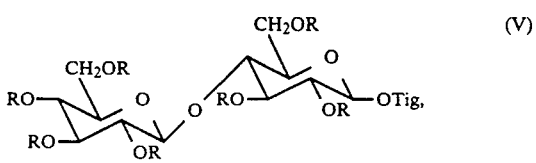

or (b') reacting said imidate of the formula (III) with tigogenin in the presence of boron trifluoride etherate in the same or another reaction-inert solvent at or about ambient temperature to form a said tigogenin beta-cellobioside heptaalkanoate of the formula (V); and (c) conventionally hydrolyzing said tigogenin beta-cellobioside heptaalkanoate to form said tigogenin beta-cellobioside.

Again, the preferred value of $R^4$ is methyl, i.e., R is acetyl.

As used above and elsewhere herein, the expression "reaction-inert solvent" refers to a solvent which does not interact with starting materials, reagents, intermediates or products in a manner which adversely affects the yield of the desired product. In general, said solvent can comprise a single entity, or contain multiple components.

DETAILED DESCRIPTION OF THE INVENTION

One key to the present invention is the stereo-specific conversion of cellobiose heptaalkanoate (II) to a key intermediate, viz., the alpha-acetimidate of the formula (III). In this conversion, the cellobiose heptaalkanoate is reacted with at least one molar equivalent (preferably a 1-10 fold molar excess) of trichloroacetonitrile in a reaction-inert solvent such as methylene chloride in the presence of a catalytic amount of cesium carbonate (e.g., about 5 mol % relative to cellobiose heptaacetate). Temperature is not critical, but the reaction is preferably carried out at or near ambient temperature so as to avoid the cost of heating or cooling. The present stereo-specific formation of the alpha-anomer with this catalyst is most surprising, since Schmidt, particularly expert in this type of transformation, recommends another alkali metal carbonate, viz., potassium carbonate as catalyst for selective formation of the undesired beta-anomer.

The resulting alpha-imidate (III) is coupled with tigogenin in a reaction-inert solvent in the presence of boron trifluoride etherate in analogy to the method of Schmidt, cited above. This coupling step, which is also conveniently accomplished at or about ambient temperature, produces known tigogenin beta-cellobioside heptaacetate (V).

We have presently discovered that use of either zinc bromide or magnesium bromide etherate as catalyst under otherwise similar conditions leads to the clean formation of an intermediate orthoester of the formula (IV). If desired, this ortho ester can be isolated. However, it is preferred to simply heat the reaction mixture to accomplish rearrangement of this ortho ester to intermediate tigogenin beta-cellobioside heptaacetate (V). It is convenient to replace any alkanoyl groups lost in this process by reaction with the appropriate alkanoic acid anhydride prior to isolation of this intermediate.

In the final step, the heptaacetate of the formula (V) is conventionally hydrolyzed or solvolyzed, e.g., according to the method of Malinow, cited above; or by the method specifically exemplified below.

The present invention is illustrated by the following examples. However, it should be understood that the invention is not limited to the specific details of these examples.

EXAMPLE 1 alpha-O-Cellobiosyl Trichloroacetimidate Heptaacetate (III, R=acetyl)

Under $N_2$, cellobiose heptaacetate (10 g, 0.0157 mol; prepared from the octaacetate according to the method of Excoffier et al., Carbohydrate Res., v. 39, pp. 368-373, 1975) was dissolved in 100 ml $CH_2Cl_2$ in a flame dried flask and cooled to 0°-5° C. Trichloroacetonitrile (4 ml) was added by syringe and then $Cs_2CO_3$ (0.52 g, 0.00158 mol) was added as a finely ground powder. The mixture, which was immediately allowed to warm to room temperature, was stirred for 5 hours, then clarified by filtration over diatomaceous earth, and the filtrate stripped, taken up in hexane/ethyl acetate and restripped to yield 11 g of title product. Recrystallization from ethyl acetate/hexane gave 6.1 g of purified title product, m.p. 192°-194° C; $^1$H-NMR(CDCl$_3$, 300 MHz)delta(ppm) 8.63 (s, 1H), 6.45 (d, 1H), 5.50 (t, 1H), 5.1 (m, 3H), 4.9 (t, 1H), 4.52 (m, 2H), 4.37 (dd, 1H), 4.07 (m, 3H), 3.82 (t, 1H), 3.65 (m, 1H), 2.10 (s, 3H), 2.07 (s, 3H), 1.97 (m, 15H).

Analysis: C 43.02, H 4.49, N 1.81; Calculated: C 43.06, H 4.65, N 1.79.

EXAMPLE 2

Orthoester Derived From alpha-O-Cellobiosyl Trichloroacetimidate Heptaacetate and Tigogenin (IV, $R^4$=CH$_3$)

Title product of the preceding Example (1.2 g, 1.54 mmol), tigogenin (0.5 g, 1.2 mmol) and molecular sieves (0.5 g, 3A type) were combined in 20 ml of $CH_2Cl_2$ at room temperature. After stirring for 10 minutes, $ZnBr_2$ (0.21 g, 0.93 mmol) was added and the mixture stirred for 1.25 hours, filtered over diatomaceous earth, the filtrate washed with 0.5M HCl, $H_2O$ and brine, dried over $MgSO_4$, stripped, and the residue slurried in hexane to yield present title product as a white solid, 0.55 g, m.p. 187.5°-188.6° C.; tlc Rf 0.3 (3:1 CHCl$_3$:ethyl acetate).

Analysis: C, 61.14; H, 7.54. Calculated: C, 61.49; H, 7.60.

Alternatively, title product was simply formed in situ by the same method, omitting the filtration and subsequent isolation steps. The formation of title product was monitored by tlc.

This ortho ester product was also produced when magnesium bromide etherate was used in place of $ZnBr_2$.

EXAMPLE 3

Tigogenin beta-Cellobioside Heptaacetate (V, R=acetyl)

Method A

Title product of the preceding Example was formed in 20 ml of $CH_2Cl_2$ from title product of Example 1 (1.15 g, 1.47 mmol) according to the procedure of the preceding Example. Monitoring by tlc demonstrated complete conversion to the orthoester within 2 hours. The ortho ester was then converted to present title product by heating the reaction mixture at reflux for 18 hours, then cooling to room temperature, adding acetic anhydride and allowing the reaction to stir for 3 hours to replace partially lost acetyl groups. To isolate and purify title product, the reaction mixture was filtered, and the filtrate washed with $H_2O$ and brine, dried ($MgSO_4$), stripped and the residue chromatographed on silica gel using 4:1 $CHCl_3$: ethyl acetate as eluant. The yield of purified title product was 0.8 g (59%), identical with the known product.

Alternatively, following treatment with acetic anhydride, the reaction mixture was filtered, washed with 0.5 N HCl, water and brine, dried ($MgSO_4$), stripped to an oil and the residue crystallized from isopropyl ether, 0.46 g (34%). Additional product (0.09 g, 7%) was obtained from mother liquors by stripping and chromatography according to the preceding paragraph.

Method B

A mixture of tigogenin (4.7 g, 0.0113 mol) and flame dried molecular seives (3A type, 10 g) and 100 ml hexane was added to a solution of title product of Example 2 (0.014 mol) in 100 ml of $CH_2Cl_2$, and the mixture stirred 18 hours at room temperature, then cooled to 0°–5° C. $BF_3\cdot(C_2H_5)O$ (0.43 ml, 0.0055 mol) in 10 ml $CH_2Cl_2$ was added dropwise over 30 minutes. After 2 hours solid $NaHCO_3$ (5 g) was added, and the mixture stirred for 10 minutes, filtered, the filtrate washed 2x saturated $NaHCO_3$ and 1x brine, dried ($MgSO_4$) and stripped to solids which were twice recrystallized from absolute alcohol to yield 5.32 g of purified title product.

EXAMPLE 4

Tigogenin beta-Cellobioside

Under $N_2$, and under anhydrous conditions, title product of the preceding Example (7.8 g, 7.53 mmol) was dissolved in 78 ml of $CH_3OH$: tetrahydrofuran 1:1 by volume. Sodium methoxide (0.020 g, 0.37 mmol) was added in one portion and the mixture heated to reflux for 1 hour. Tetrahydrofuran was removed by distillation to a head temperature 62° C. Fresh methanol (80 ml) was added and distillation continued to a head temperature of 65° C. Water (8 ml) was added and the mixture reheated to reflux, seeded, digested at reflux for 2.5 hours, cooled slowly with stirring to room temperature, stirred overnight and present title product recovered by filtration, 4.21 g, identical with the known product.

I claim:

1. A compound of the formula

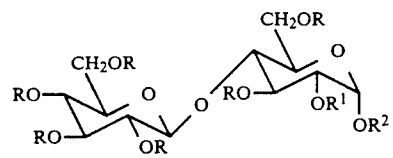

wherein
R is $R^4CO$;
$R^1$ and $R^2$ are taken together and are

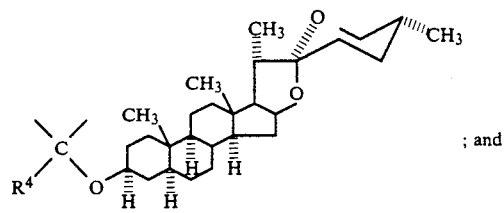
; and $R^4$ is $C_1$–$C_4$ alkyl.

2. The compound of claim 1 wherein $R^1$ and $R^2$ are taken together, R is acetyl, and $R^4$ is methyl.

3. A process for the synthesis of tigogenin beta-cellobioside which comprises the steps of
(a) reacting a cellobiose heptaalkanoate of the formula

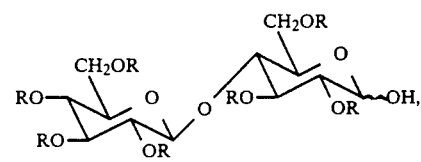

wherein
R is $R^4CO$ and $R^4$ is ($C_1$–$C_4$)alkyl, with trichloroacetonitrile in the presence of a catalytic amount of cesium carbonate in a reaction-inert solvent at or about ambient temperature to form an imidate of the formula

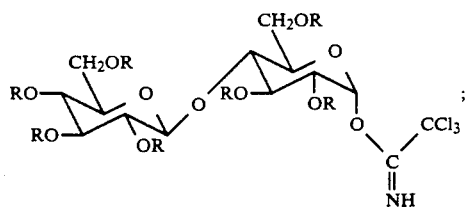

(b) reacting said imidate with tigogenin in the presence of zinc bromide or magnesium bromide etherate in the same or another reaction-inert solvent at or about ambient temperature to form an orthoester of the formula

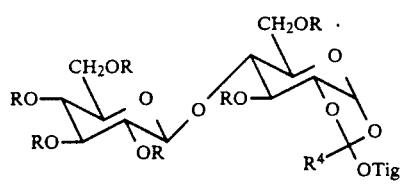

wherein Tig is

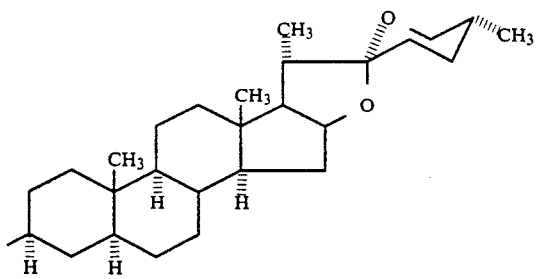

(c) heating said orthoester in the same or another reaction-inert solvent to form a tigogenin beta-cellobioside heptaalkanoate of the formula

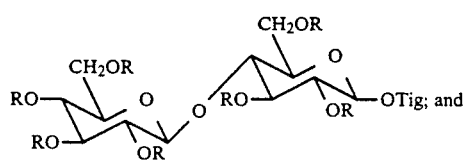

(d) hydrolyzing said tigogenin beta-cellobioside heptaalkanoate to form said tigogenin beta-cellobioside.

4. A process of claim 3 wherein R is acetyl and $R^4$ is methyl.

5. A process for the synthesis of an imidate of the formula

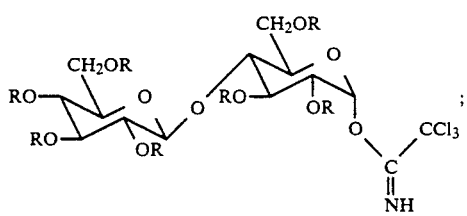

wherein R is $(C_2-C_5)$alkanoyl, which comprises reacting a cellobiose heptaalkanoate of the formula

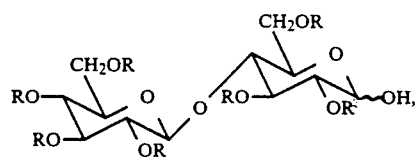

wherein R is $(C_2-C_5)$alkanoyl with trichloroacetonitrile in the presence of a catalytic amount of cesium carbonate in a reaction-inert solvent at or about ambient temperature.

6. A process of claim 5 wherein R is acetyl.

7. A process for the synthesis of an orthoester of the formula

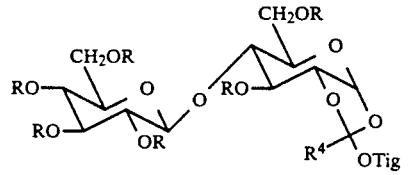

wherein
R is $R^4CO$;
$R^4$ is $(C_1-C_4)$alkyl; and
Tig is

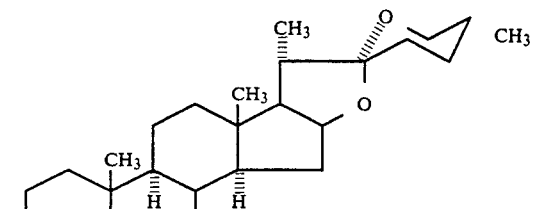

which comprises reacting an imidate of the formula

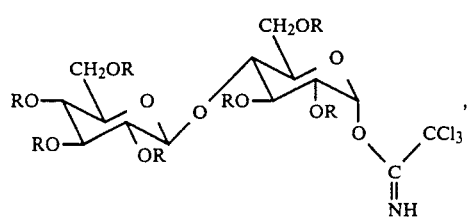

with tigogenin in the presence of zinc bromide or magnesium bromide etherate in a reaction-inert solvent at or about ambient temperature.

8. A process of claim 7 wherein R is acetyl and $R^4$ is methyl.

9. A process of claim 7 which further comprises heating said orthoester in the same or another reaction-inert solvent to form a tigogenin beta-cellobioside heptaalkanoate of the formula

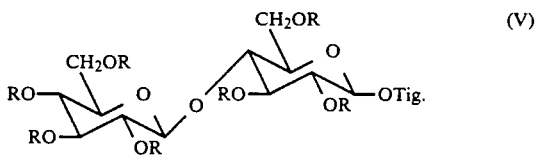

10. A process of claim 9 which further comprises hydrolyzing said tigogenin beta-cellobioside heptaalkanoate to form tigogenin beta-cellobioside.

11. A process of claim 9 wherein $R^4$ is methyl.

12. A process of claim 10 wherein $R^4$ is methyl.

13. A process for the synthesis of tigogenin beta-cellobioside which comprises the steps of (a) reacting a cellobiose heptaalkanoate of the formula

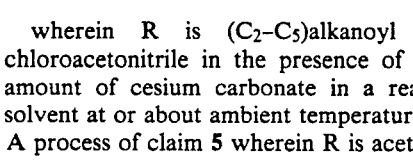

wherein R is $(C_2-C_5)$alkanoyl, with trichloroacetonitrile in the presence of a catalytic amount of cesium carbonate in a reaction-inert solvent at or about ambient temperature to form an imidate of the formula

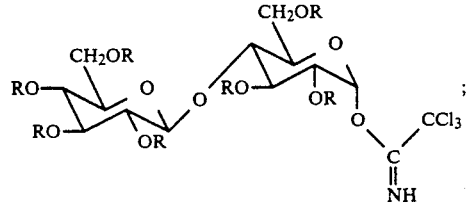

(III)

(b) reacting said imidate with tigogenin in the presence of boron trifluoride etherate in the same or another reaction-inert solvent at or about ambient temperature to form a tigogenin beta-cellobioside heptaalkanoate of the formula

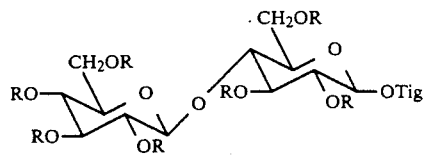

(V)

wherein Tig is

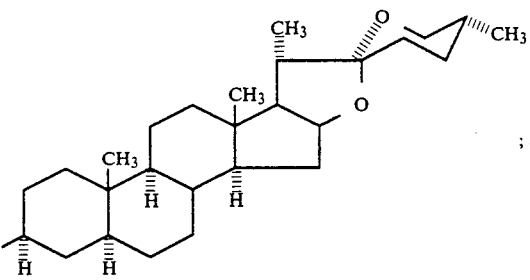

; and (c) hydrolyzing said tigogenin beta-cellobioside heptaalkanoate to form said tigogenin beta-cellobioside.

14. A process of claim 13 wherein R is acetyl.

* * * * *

UNITED STATES PATENT AND TRADEMARK OFFICE
CERTIFICATE OF CORRECTION

PATENT NO. : 5,010,185
DATED : April 23, 1991
INVENTOR(S) : Frank J. Urban

It is certified that error appears in the above-identified patent and that said Letters Patent is hereby corrected as shown below:

Column 2, line 41, "formula (I)" should read -- formula (III) --.

Column 6, line 21, "$C_1-C_4$)alkyl" should read -- ($C_1-C_4$)alkyl --.

Signed and Sealed this

Sixth Day of July, 1993

Attest:

MICHAEL K. KIRK

Attesting Officer     Acting Commissioner of Patents and Trademarks